US00PP10761P

United States Patent [19]

Button

[11] Patent Number: Plant 10,761

[45] Date of Patent: Jan. 19, 1999

[54] AGLAONEMA PLANT NAMED 'FRAN HANAN'

[75] Inventor: Richard John Button, Coral Gables, Fla.

[73] Assignee: Sunshine Foligage World, Zolfo Springs, Fla.

[21] Appl. No.: 929,491

[22] Filed: Sep. 15, 1997

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 9,993 8/1997 Lamb et al. ..... Plt./88.1

*Primary Examiner*—Howard J. Locker
*Assistant Examiner*—Kent L. Bell
*Attorney, Agent, or Firm*—C. A. Whealy

[57] ABSTRACT

A new and distinct cultivar of Aglaonema named 'Fran Hanan' particularly characterized by its upright growth habit; large plant size; pink leaf petioles; grayed green upper leaf surfaces with very dark green spots, streaks, splotches and margins; and green lower leaf surfaces with pronunced white venation.

2 Drawing Sheets

The present invention relates to a new and distinct cultivar of Aglaonema plant, botanically known as Aglaonema hybrid, and hereinafter referred to by the cultivar name 'Fran Hanan'.

The new Aglaonema is a product of a planned breeding program conducted by the inventor in Coral Gables, Fla. The objective of the breeding program was to develop large Aglaonemas with pink-colored leaf petioles. The new Aglaonema originated from a cross made by the inventor of the Aglaonema hybrid cultivar 'Penny' (U.S. Plant Pat. No. 9,993) as the female, or seed, parent with a proprietary selection of the species *Aglaonema marantifolium tricolor* as the male, or pollen, parent. The cultivar 'Fran Hanan' was discovered and selected by the inventor as a seedling within the progeny of the stated cross in a controlled environment in Coral Gables, Fla.

Asexual propagation of the new cultivar by divisions at Zolfo Springs, Fla., since 1991, has shown that the unique features of this new Aglaonema plant are stable and reproduced true to type in successive generations.

The new Aglaonema has not been observed under all possible environmental conditions. The phenotype may vary somewhat with variations in environment such as temperature, light intensity, fertilizer rate, and/or irrigation amount and frequency without, however, any variance in genotype.

The following traits have been repeatedly observed and are determined to be the unique characteristics of 'Fran Hanan'. These characteristics in combination distinguish 'Fran Hanan' as a new and distinct cultivar:

1. Plants of the new Aglaonema are upright in growth.
2. Plants of the new Aglaonema are relatively large and slow-growing compared to other commercial Aglaonema cultivars.
3. Leaf petioles of plants of the new Aglaonema are pink in color.
4. The upper surfaces of mature leaves of plants of the new Aglaonema are grayed green with very dark green spots, streaks, splotches and margins.
5. the lower surfaces of mature leaves of plants of the new Aglaonema are green with pronounced white venation.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of three typical plants of 'Fran Hanan' in a 36-cm container.

The photographs on the second sheet comprise close-up views of the upper surface of a mature leaf (top) and the lower surface of a mature leaf (bottom). Leaf colors in the photographs may appear different from the actual colors due to light reflectance.

DETAILED BOTANICAL DESCRIPTION

The following observations, measurements and comparisons describe plants grown in Zolfo Springs, Fla., under a polypropylene-covered shadehouse and conditions which closely approximate those used in horticultural practice. Plants were grown under day temperatures ranging from 21° to 38° C. and night temperatures ranging from 7° to 21° C. The polypropylene shade provided a 84 percent decrease in ambient light level. In the following description, color references are made to The Royal Horticultural Society Colour Chart except where general terms of ordinary dictionary significance are used.

Botanical classification: Aglaonema hybrid cultivar Fran Hanan.

Parentage:

*Female, or seed, parent.*—Aglaonema hybrid cultivar 'Penny', U.S. Plant Pat. No. 9,993.

*Male, or pollen, parent.*—Proprietary selection of the species *Aglaonema marantifolium tricolor.*

Propagation:

*Type.*—By division and by cuttings.

*Time to initiate roots.*—About 14 and 30 days at 27° and 16° C., respectively.

*Time to develop roots.*—About 21 and 60 days at 27° and 16° C., respectively.

*Rooting habit.*—Numerous thick, fleshy, white roots.

Plant description:

*Plant shape.*—Mostly upright and somewhat outwardly arching and spreading, symmetrical. Numerous and closely-spaced large leaves give plants a full and dense appearance.

*Growth habit.*—Erect when young, becoming more outwardly arching and spreading. Appropriate for 25-cm and larger containers.

*Plant size.*—Height, soil surface to top of leaf canopy: About 110 cm. Width: About 110 cm.

*Plant vigor.*—Vigorous, but slow growth rate.

*Stem description.*—Diameter at soil surface: About 4 cm. Internode length: About 2.75 cm. Color, mature: Light green.

*Foliage description.*—Leaf shape: Oblong. Leaf length, fully expanded: About 40 cm. Leaf width, fully expanded: About 20 cm. Margin: Entire. Leaf tip: Acuminate. Leaf base: Obtuse. Leaf aspect: Flat to curved downward. Leaf texture: Leathery; smooth and glabrous; both surfaces somewhat glossy. Leaf color: Young, upper surface: Background: 146C to 137C. Midrib: Apex, 146A to darker than 147A; towards base, yellowish green. Margin, spots/streaks: 146A to darker than 147A. Young, lower surface: Background: 146C to 146B. Midrib: Light green to whitish; laterals, whitish. Margin, spots/streaks: Not apparent. Mature, upper surface: Background: Closest to 189A. Midrib: Apex, darker than 147A; towards base, yellowish green. Margin, spots/streaks; Much darker than 147A. Mature, lower surface: Background: Close to 147B. Midrib: Whitish; laterals, whitish. Margin, spots/streaks: Not apparent. Petiole length, primary shoot: About 30 cm. Petiole diameter at apex: About 8 mm. Petiole diameter at base: About 3.6 cm. Petiole wing: Apparent on lower 60% of mature leaf petiole, about 18 cm in length and about 1 cm in width. Petiole color: Young: White, 155D, with pink overtones. Petioles appear pink. Wings: Speckled with 147A. Mature: White, 155D, with pink overtones. Petioles appear pink.

*Inflorescence.*—Typical of Aglaonema, no commercial significance.

Disease tolerance: Plants of the new Aglaonema are relatively resistant to diseases common to Aglaonema.

It is claimed:

1. A new and distinct cultivar of Aglaonema plant named 'Fran Hanan', as illustrated and described.

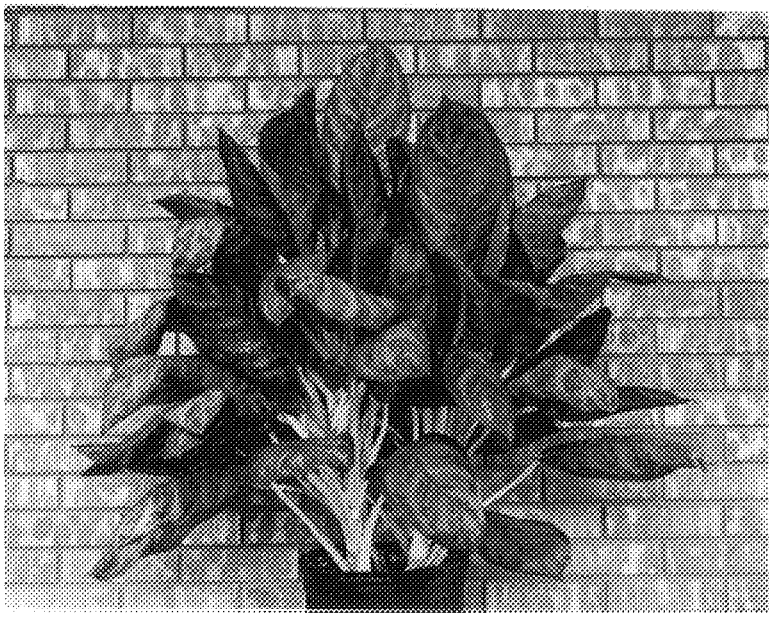

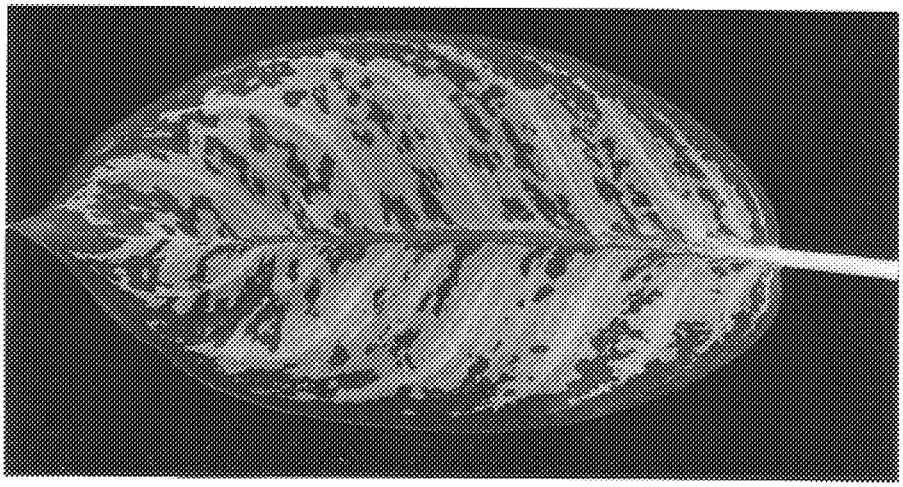
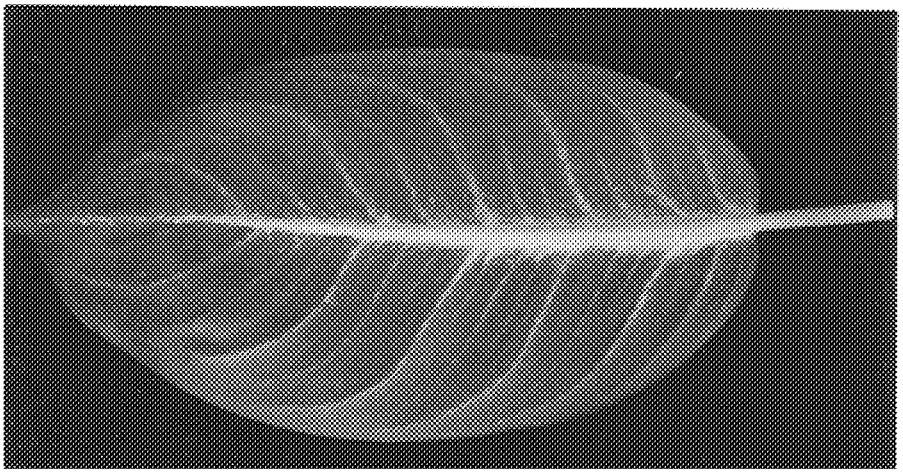

* * * * *